United States Patent [19]

Eilerman et al.

[11] Patent Number: 5,147,463

[45] Date of Patent: Sep. 15, 1992

[54] CYCLIC ACETALS

[75] Inventors: Robert G. Eilerman, Merrick, N.Y.; Philip A. Christenson, Midland Park, N.J.; John M. Yurecko, Jr., Dayton, N.J.; Frank Mild, Westwood, N.J.; Peter E. Kucharski, Yardley, Pa.

[73] Assignee: BASF K&F Corporation, Whippany, N.J.

[21] Appl. No.: 395,628

[22] Filed: Aug. 18, 1989

[51] Int. Cl.$^5$ .................. A24B 3/12; C07D 31/02
[52] U.S. Cl. ................................ 131/277; 549/365
[58] Field of Search ............... 131/276, 277; 549/365

[56] References Cited

FOREIGN PATENT DOCUMENTS 109281 11/1987 Japan .
211391 12/1988 Japan .

OTHER PUBLICATIONS

Wood, Harry B. et al., "1,2,:4,6-Di O-benzylidene α-D-glucopyranose and Improvements in the Preparation of 4,6-O-Benzylidene-D-glucopyranose" J. Am. Chem. Soc. 79:1986 (1957).
Joniak, D. et al., "Preparation of some methyl-D-glucopyranoside cyclic acetals by transacetylation":, Chem. zesti 31(1) 106–108 (1977).
Jedlinski, Z. et al., "The Synthesis, Structure and Properties of Some Unsaturated Methyl-D-Hexapyranoside Acetals: Univ. Adama. Miekiewicza Pozhaniu, Wydz. Mzt., Fiz." Chem. [Pr], Ser. Chem. 18.

Primary Examiner—V. Million
Attorney, Agent, or Firm—Kenyon & Kenyon

[57] ABSTRACT

This invention provides novel cyclic acetals useful as delayed release flavorants and odorants having the general formula:

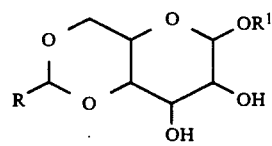

These compounds possess no detectable flavor or odor themselves at normal temperatures and atmospheric conditions but release an aldehyde flavorant upon heating at higher temperatures. The novel cyclic acetals of the present invention may be used as flavorants in tobacco compositions or tobacco substitutes, as sustained flavorants and odorants to mask or enhance the flavors and odors of burning tobacco products, as flavor additives to microwaveable foods, and in the preparation of chewing gums.

32 Claims, No Drawings

CYCLIC ACETALS

FIELD OF THE INVENTION

This invention relates to novel cyclic acetals useful as delayed release flavorants and odorants. The invention also provides a process for the synthesis of these compounds as well as smoking and flavorant compositions which incorporate the invention. The compounds of the invention are used as sustained release odorants which are incorporated in the media enclosing the tobacco. They may also be used as flavor additives to microwaveable foods.

BACKGROUND OF THE INVENTION

Flavor additives have long been used to flavor a wide variety of consumer products, particularly tobacco products, foodstuffs, and gums. Flavor additives in such products may be used to mask or attenuate undesirable flavors or odorants, and to enhance existing flavors or odors, or to provide additional flavors or odors not initially present in the consumer product.

A principal strategy currently employed to impart flavors or odors to consumer products is the admixing of the flavorant chemicals within a matrix that slows or prevents their release until the product is pyrolyzed, heated, masticated or wetted. Alternatively, the flavoring chemical may be covalently bound to an auxilliary component to form a higher weight molecule of low volatility. The flavorant is then released upon pyrolysis, heating or solvolysis of the tobacco or food product.

For example, European patent 186,502 describes the use of a plastic capsule that releases flavorants when mechanically crushed.

U.S. Pat. No. 4,001,438 describes flavor compositions for use in orally utilizable compositions which may be either chewing gum compositions, chewable medicinal tablets, chewing tobacco or toothpaste. The flavor is controllably released from the flavor compositions over an extended period of time under hydrolytic conditions.

U.S. Pat. No. 4,253,473 describes smoking tobacco compositions or substitute smoking tobacco compositions which upon smoking release substantially evenly and uniformly over an extended period of time.

U.S. Pat. No. 3,818,107 describes a chewing gum containing a flavor release composition comprising polymer backbones with flavor groups appended thereto. The flavor moieties are released from the polymer backbone by hydrolysis which is achievable by mastication of chewing gums containing the flavor groups.

As an alternative method, the flavoring chemicals may be covalently bound to an auxilliary component to form a higher molecular weight molecule of low volatility. The flavorant is released upon pyrolysis, heating or solvolysis of the tobacco or food product.

In general, inventions employing the second strategy use an ester or carbonate linkage of a higher molecular weight molecule to an alcoholic flavor molecule. In such a system a flavor molecule is covalently bound to a polymer and may be depicted by the following generalized structure:

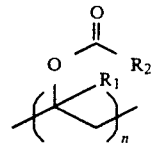

wherein $R_1$ represents a low alkyl group such as methyl, $R_2$ represents a flavorant radical such as menthyl and n is an integer from 2 to 10,000. This approach has been demonstrated in a number of U.S. Patents. For example, U.S. Pat. No. 4,212,310 describes different flavored smoking tobacco products wherein some of the products contain an alcohol flavorant-release composition which delivers the flavor note of the alcohol upon pyrolysis.

U.S. Pat. No. 4,119,106 describes alcohol flavorant-release polymeric derivatives which are designed to enhance tobacco smoke by releasing an alcohol flavorant to tobacco smoke without wasting the natural flavor of the resultant main stream tobacco smoke.

U.S. Pat. Nos. 4,578,486 and 4,538,628 describe smoking tobacco compositions which contain dioxane diester flavorant-release additives. When subjected to normal smoking conditions such as cigarettes, the diester additive decomposes to release a volatile pyrolysis (alcohol or phenol) component which provides flavor-enhancing properties to the mainstream smoke and enhances the aroma of the sidestream smoke.

U.S. Pat. Nos. 4,701,282, 4,538,627 and 4,540,004 describe the use of ketoester or carbonate ester compounds as flavorant additives which under cigarette smoking conditions pyrolyze to release flavorants which enhance the flavor of the mainstream smoke and the aroma of sidestream smoke.

Acetals have also been used as vehicles to covalently bind aldehyde flavorants. For example, U.S. Pat. No. 4,296,137 describes the use of 1-ethoxy-1-ethanol acetate or a flavor or fragrance enhancer of a wide variety of consumable materials. The 1-ethoxy-1-ethanol acetate compound has the ability to liberate acetaldehyde in smoking tobacco. U.S. Pat. No. 4,280,011 describes the use of acetals as aldehyde generators in foodstuff applications. U.S. Pat. No. 3,625,709 describes food flavoring and aroma enhancers consisting of acetaldehyde combined with carbohydrates to form compositions which release acetaldehyde when combined with hot water or with cold water. U.S. Pat. No. 4,857,964 describes controlled release flavor compositions useful in flavor compositions which comprise flavor particles formed from a dispersion of flavor acetal or ketal in polymeric binders. The controlled release flavor compositions have multiple means of control, one of which is the hydrolysis of the flavor acetal or ketal. These controlled release flavor compositions are useful in chewing gums.

Finally, U.S. Pat. Nos. 4,690,157 and 4,607,118 describe tobacco compositions which contain flavor release additives which, under cigarette smoking conditions, pyrolyze in a "retro-aldol" fragmentation reaction into products which enhance the flavor and aroma of the cigarette smoke.

It is one object of the present invention to provide a series of novel compounds, as well as methods for their synthesis, useful as flavorants and as sustained release odorants to mask and/or to enhance the odors of burning tobacco products.

Another object of the present invention is to flavor cooked foods, e.g., microwaveable foods, which, during the cooking process, release flavorants into the food.

Yet another object of the present invention is to flavor chewing gum.

SUMMARY OF THE INVENTION

In accordance with the above-mentioned objects and other objects, the following invention is directed to the class of novel cyclic acetal compounds having the formula:

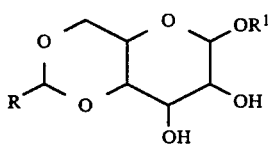
I where $R^1$ is H or $C_1$ to $C_6$ alkyl;

R is Ar or $Ar^1$, with Ar equal to 3-ethoxy-4-hydroxyphenyl or 5-methylthiophen-2-yl, and $Ar^1$ equal to

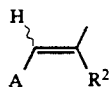

with A representing phenyl, 4-methoxyphenyl or 3-methoxy-4-hydroxyphenyl, such that when A is phenyl, $R^2$ is $C_1$ to $C_6$ alkyl; when A is 4-methoxyphenyl, $R^2$ is H or $C_1$ to $C_6$ alkyl, and when A is 3-methoxy-4-hydroxyphenyl, $R^2$ is H.

The invention described herein further encompasses a method of flavoring a food comprising adding to a foodstuff an effective amount of a compound of formula Ia:

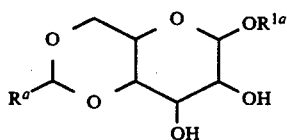
Ia where $R^{1a}$ is H or $C_1$ to $C_6$ alkyl;

$R^a$ is $Ar^a$ or $Ar^{1a}$, where $Ar^a$ represents 3-ethoxy-4-hydroxyphenyl, 3-methoxy-4-hydroxyphenyl, 4-methoxyphenyl or heteroaryl, and $Ar^{1a}$ is

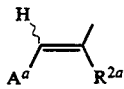

with $A^a$ representing phenyl, 4-methoxyphenyl, 3-methoxy-4-hydroxyphenyl or heteroaryl, and $R^{2a}$ represents H or $C_1$ to $C_6$ alkyl.

The invention described herein further encompasses a method of flavoring tobacco or tobacco paper comprising adding to said tobacco or tobacco paper an effective amount of a compound of formula Ib:

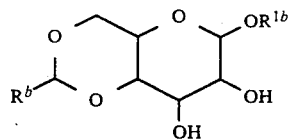
Ib where $R^{1b}$ is H or $C_1$ to $C_6$ alkyl;

$R^b$ is $Ar^b$ or $Ar^{1b}$, with $Ar^b$ equal to 3-ethoxy-4-hydroxyphenyl, 3-methoxy-4-hydroxyphenyl, 4-methoxyphenyl, 3,4-methylenedioxyphenyl or heteroaryl, and $Ar^{1b}$ is

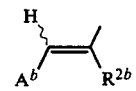

with $A^b$ representing phenyl, 4-methoxyphenyl, 3-methoxy-4-hydroxyphenyl, 3,4-methylenedioxyphenyl or heteroaryl and $R^{2b}$ is H or $C_1$ to $C_6$ alkyl.

DETAILED DESCRIPTION

As used herein the term "organoleptic" refers to compounds of the invention which stimulate the sense of smell or taste, and are thus perceived as having a characteristic odor and/or flavor.

The terms "odor", "fragrance" and "smell" are used interchangeably whenever a compound is referred to as an organoleptic which is intended to stimulate the sense of smell.

The terms "flavor", "flavoring" and "flavorant" are also used interchangeably whenever and organoleptic compound is referred to which in intended to stimulate the sense of taste.

An "organoleptically effective amount" is a level or amount of a novel cyclic acetal compound(s) present in a material at which the incorporated compound(s) exhibit(s) a sensory effect.

The terms "tobacco" and "tobacco substitutes" are used in the conventional sense and include smokable as well as non-smokable forms in which tobacco is regularly used, e.g., cigarettes, snuff, chewable compositions, etc.

The term "tobacco paper" refers to smokable paper used to contain tobacco, e.g., tobacco rolling paper.

The following chemical terms are used throughout the specification, and are defined as follows unless otherwise indicated:

Acetal—an organic compound formed by addition of an alcohol to an aldehyde.

Alkyl (including the alkyl portion of alkoxy, alkylthio aralkyl and heteroaralkyl)—branched or unbranched saturated carbon chain containing 1 to 20 carbon atoms, with lower alkyl representing a chain containing 1 to 6 carbon atoms.

Heteroaryl—aromatic group having 5 to 6 atoms in a ring, 1 to 3 of which are heteroatoms contained in the aromatic ring, selected from O, S or N, with the remaining atoms being carbon atoms, the group being sufficiently unsaturated to provide aromatic character to the ring.

Preferred compounds falling within the scope of the invention include those compounds where Ar, $Ar^a$ and $Ar^b$ are 3-ethoxy-4-hydroxyphenyl, and where A, $A^a$ and $A^b$ are phenyl.

The preferred value of $R^1$, $R^{1a}$ and $R^{1b}$ is H.

Compounds falling within the scope of formula I which are preferred include:

methyl 4,6-0-(4-hydroxy-3-ethoxybenzylidene) glucopyranoside;

methyl 4,6-0-[3-(3-methoxy-4-hydroxyphenyl)prop-2-enylidene]glucopyranoside;

methyl 4,6-0-(5-methylthiophene-2-methylide) glucopyranoside;

methyl 4,6-0-[3-(4-methoxyphenyl)prop-2-enylidene]glucopyranoside;

methyl 4,6-0-(3-phenyl-2-pentylprop-2-enylidene) glucopyranoside, and methyl 4,6-0-(3-phenyl-2-hexylprop-2-enylidene) glucopyranoside.

Preferred compounds for use in flavoring foods and beverages include those compounds recited above which fall within the scope of formula I, plus the following compounds falling within the scope of formula Ia:

methyl 4,6-0-(3-methoxy-4-hydroxybenzylidene) glucopyranoside;

methyl 4,6-0-(4-methoxybenzylidene) glucopyranoside;

methyl 4,6-0-(3-phenylprop-2-enylidene) glucopyranoside;

methyl 4,6-0-(3-(4-methoxyphenyl)prop-2-enylidene) glucopyranoside;

methyl 4,6-0-(3-(3-methoxy-4-hydroxyphenyl) prop-2-enylidene)glucopyranoside; and methyl 4,6-0-(3-furanylprop-2-enylidene)-glucopyranoside.

Preferred compounds useful for flavoring tobacco or tobacco paper include, in addition to the compounds recited above falling within the scope of formulae I and Ia, the following compounds falling within the scope of formula Ib:

methyl 4,6-0-(3,4-methylenedioxybenzylidene) glucopyranoside, and methyl 4,6-0-(3-(3,4-methylenedioxyphenyl)prop-2-enylidene)glucopyranoside.

The compounds described herein may exist in several isomeric forms. The present invention includes both essentially pure isomeric forms as well as mixtures thereof.

The novel cyclic acetals of the present invention may be used as flavorants in tobacco compositions, as sustained release odorants to mask or enhance the odors of burning tobacco products, as flavor additives for microwaveable foods, and in the preparation of chewing gums.

Under normal temperature and atmospheric conditions the cyclic acetals exist as stable solids which have no detectable odor. Upon heating to higher temperatures or upon chewing, as in the case of a chewing gum, the flavorant is released.

The novel cyclic acetal compounds of the present invention are substantially odorless and tasteless under normal temperatures and atmospheric conditions, e.g., about 10°–50° C. and about 20 to 100% relative humidity, and exist as stable solids. However, when heated to higher temperatures, e.g., about 70° C. to about 300° C., in the presence of moisture or steam, they undergo a transformation in which the odor or flavor is released. This transformation may be represented by the following Scheme I.

$$\text{I} \longrightarrow \text{RCHO}$$

$$\text{II}$$

($R^1$ = H or lower alkyl of 1–3 carbon atoms;

The aromatic aldehyde obtained from the transformation of Scheme I is useful as a flavorant or odorant.

Illustrative structures of species which can be made in accordance with the teachings herein are shown below in Table I.

TABLE I

III — methyl 4,6-0-(4-hydroxy-3-ethoxybenzylidene) glucopyranoside

IV — methyl 4,6-0-(3,4-methylenedioxybenzylidene) glucopyranoside

TABLE I-continued

| | |
|---|---|
|  V | methyl 4,6-O-(4-methoxy-benzylidene) glucopyranoside |
| 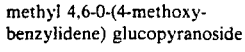 VI | methyl 4-6-O-(4-hydroxy-3-methoxybenzylidene) glucopyranoside |
|  VII | methyl 4,6-O-(5-methylthiophenemethylide) glucopyranoside |
| 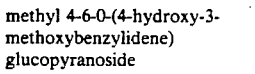 VIII | methyl 4,6-O-(3-phenylprop-2-enylidene) glucopyranoside. |
|  IX | methyl 4,6-O-[3-(4-methoxyphenyl)prop-2-enylidene] glucopyranoside. |
| 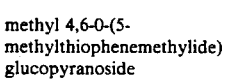 X | methyl 4,6-O-(3-phenyl-2-pentylprop-2-enylidene) glucopyranoside |
| 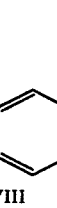 XI | methyl 4,6-O-(3-phenyl-2-hexylprop-2-enylidene) glucopyranoside |

The cyclic acetals according to structure Ia may be prepared by the reaction of the flavorant with a pyranoside as shown in the following scheme II.

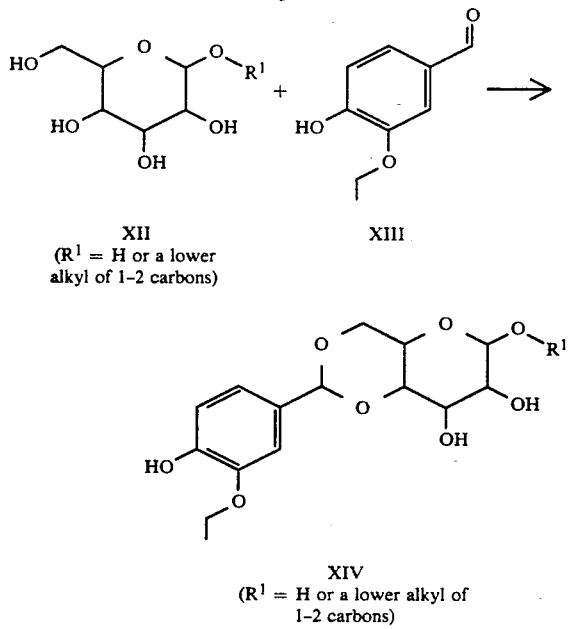

XII
($R^1$ = H or a lower alkyl of 1-2 carbons)

XIII

XIV
($R^1$ = H or a lower alkyl of 1-2 carbons)

According to Scheme II, a pyranoside XII is reacted with the flavorant ethyl vanillin XIII in the presence of a suitable solvent, acid catalyst and dehydrating agent. The preferred solvents are aprotic solvents such as acetonitrile, dimethyl acetamide, methylene chloride, N-methylpyrrolidone, 1,2-dichloroethane, toluene and xylene. The more preferred solvent is dimethylformamide. The preferred acid catalysts include sulfuric acid, nitric acid, trifluoroacetic acid, boron trifluoride, hydrochloric acid, methanesulfonic acid, zinc chloride, magnesium chloride and magnesium bromide. The more preferred acid catalyst is p-toluenesulfonic acid. The more preferred dehydrating agents include triethylorthoformate, trimethylorthoacetate, magnesium sulfate (anhydrous) and sodium sulfate (anhydrous). The more preferred dehydrating agent is triethylorthoformate. A dehydrating process involving the azeotropic removal of water using a solvent such as toluene may also be used.

Compounds of formulae Ia and Ib are prepared in accordance with the above teachings, taking into account the examples contained herein.

The cyclic acetal compounds of the invention possess organoleptic properties and therefore permit the development of methods useful in enhancing the flavor of foods. These compounds are also useful in enhancing the odor, masking any unpleasant odor or enhancing the flavor of tobacco products.

These compounds may be used individually in an amount effective to enhance a characteristic flavor or odor of a material. More commonly, however, the compounds are mixed with other flavor or fragrance components in an amount sufficient to provide the desired flavor or odor characteristic.

The amount required to produce the desired, overall effect varies depending upon the particular compound chosen, the product in which it will be used, and the particular effect desired.

For example, depending upon the selection and concentration of the cyclic acetals used, addition of the cyclic acetals either singly or as a mixture to cigarette tobacco at levels ranging from about 5 ppm to about 50,000 ppm tends to enhance the smoking flavor and/or mask undesirable smoking odors. An important property of these cyclic acetals is that the flavorant or odorant is covalently bound as a non-volatile compound and it is only when the tobacco product is ignited and burns that the flavorant or odorant is released.

Addition of the cyclic acetals of formula I either separately or as a mixture at levels ranging from about 5 ppm to about 50,000 ppm by weight onto the media enclosing the tobacco serves to incorporate the odorant/flavorant in the side-stream smoke as the tobacco product burns. Air borne flavorants and/or odorants along with other combustion products are thus introduced. This newly formed odorant or flavorant serves to enhance or mask the smoking odors depending upon selection and use levels of the cyclic acetals.

The cyclic acetals of the present invention are particularly useful in the flavoring and aromatizing of cooked foods. Addition of the cyclic acetals either singly or as a mixture to a cake batter, e.g., a microwave cake batter, serves to impart appropriate baking aromas to the cake as it is heated in the microwave as well as impart flavoring in the finished product. Typically, the cyclic acetals are employed at levels ranging from about 0.05 to about 5.00%.

The flavor of chewing gum may also be enhanced by the addition of cyclic acetals of formula I. A selected cyclic acetal or mixture of cyclic acetals is kneaded into a gum base at levels ranging from about 0.1% to about 10.0% by weight. The appropriate flavors are released in the resulting gum upon mastication.

The compounds of the invention may be incorporated in the foodstuff or tobacco product along with other ingredients. Such other ingredients include emulsifiers, carriers, binders, sweeteners, stabilizers, buffers and solvents.

The following examples are given to illustrate embodiments of the invention as it is preferred to practice it. It will be understood that these examples are illustrative and the invention is not to be considered to be restricted thereto.

All parts, proportions, percentages, and ratios used herein are by weight unless otherwise indicated.

EXAMPLE 1

Methyl 4,6-0-(4-Hydroxy-3-Ethoxybenzylide) Glucopyranoside

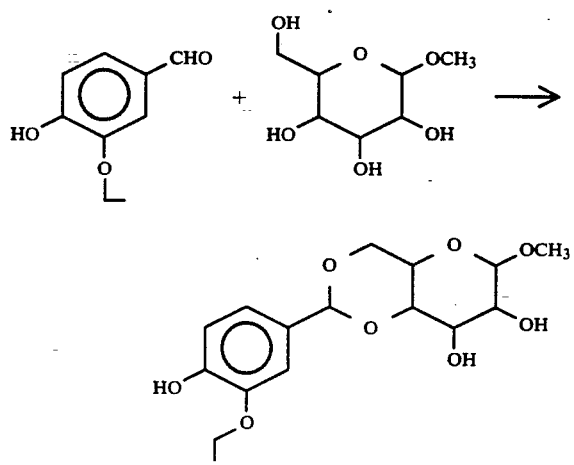

Ethyl vanillin (21.5 g, 0.13 mol), methyl glucopyranoside (25.0 g, 0.13 mol), acetonitrile (100 mL), trimethylorthoformate (15.4 g, 0.15 mol) and p-toluenesulfonic acid (0.2 g) were combined in a 500 mL round bottom flask and heated for 18 hours at reflux. Ethyl acetate (500 mL) was added to the warm solution which was washed with brine, then saturated sodium bicarbonate solution. The mixture was dried ($Na_2SO_4$), concentrated to a final volume of 200 mL and allowed to stand at 0° C. The resulting crystals were collected and dried to yield the product. mp 178°–180° C., $[\alpha]^D{}_{20}= +72.80$.$H^1$-NMR ($CD_3OD$) δ7.06 (1H,J=1.8 Hz), 26.93 (dd, 1H, J=8.4, 1.8 Hz), 6.77 d, 1H, J=8 Hz), 5.47 (s,1H), 4.7 (d, 1H, J=4.0 Hz), 4.28–4.00 (m, 3H), 3.87–3.62 (m, 3H), 3.54–3.46 (m, 1H), 3.42 (s, 3H), 3.34–3.26 (m, 2H), 1.40 (t, 3H, J=7.0 Hz). $^{13}C$ NMR ($CD_3OD$) δ148.6, 17.7, 130.8, 120.7, 115.8, 112.8, 103.2, 102.0, 82.8, 74.1, 72.1, 70.0, 65.8, 63.9, 55.8, 15.1, IR (KBr), 3530, 3420, 3310, 2925, 2860, 1660, 1512, 1437, 1415, 1370, 870 cm$^{-1}$, MS m/e (% abundance) 343 (8), 342 (38), 167 (68), 166 (100), 138 (60), 109 (28), 87 (20), 45 (75).

EXAMPLE 2

Methyl 4,6-0-(3-Phenylprop-2-Enylidene)Glucopyranoside

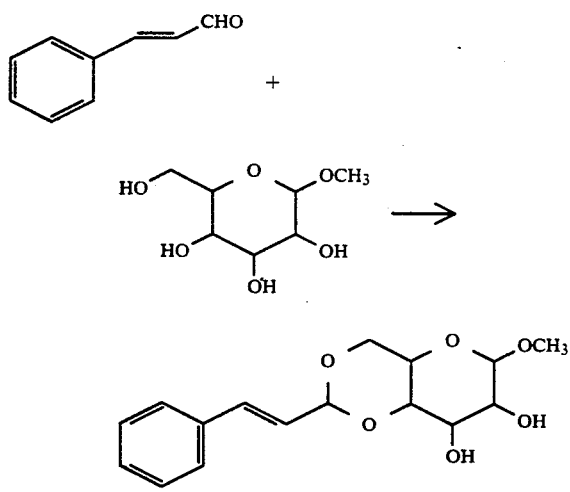

A mixture of cinnamic aldehyde (3.2 kg, 24.2 mol), methyl glucopyranoside (4.7 kg. 24.2 mol), dimethyl formamide (16L), trimethylorthoformate (2.8 kg, 26.6 mol) and p-toluenesulfonic acid monohydrate (80 g) was heated at 95° C. for 4 h. The mixture was neutralized with 40% sodium hydroxide solution. Most of the solvents were removed under reduced pressure. The residue was taken-up in ethyl acetate (12L) and the resulting solution was washed with brine. Concentration of the solution and crystallization provided the product. mp 147°–149° C., $[\alpha]_D$ 104°. $^1$H-NMR ($CD_3OD$) δ7.5–7.2 (m,5h), 6.84(d,1H, J=16.7 Hz), 6.20 (dd,1H, J=16.7 Hz and 4.0 Hz), 5.20 (d, 1H, J=4.7 Hz), 4.72 (d, 1H, J=4.0 Hz), 4.10–4.25 (m, 1H), 3.87–3.0 (m,5H), 3.43 (s, 3H). $^{13}$C-NMR (CD3OD) δ137.5, 134.9, 129.6, 129.2, 127.7, 125.9, 102.2, 102.0, 82.5, 74.2, 72.1, 69.7, 63.9, 55.8, IR (KBr) 3300, 1660, 1595, 1575, 1480, 1450 cm$^{-1}$. MS m/e (% abundance) 309 (2), 308 (12), 144 (12), 131 (40), 104 (100), 74 (22, 45 (70).

EXAMPLE 3

Methyl 4,6-0-(4-Methoxybenzylidene) Glucopyranoside

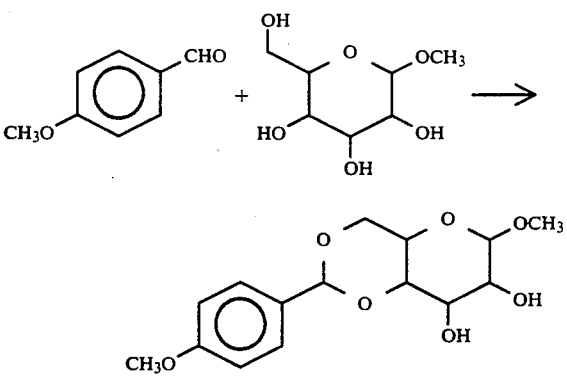

In a fashion similar to the procedure described in Example 2, anisic aldehyde and methyl glucopyranoside are combined to form methyl 4,6-O-(4-methoxybenzylidene) glucopyranoside. mp 209°–210° C., $[\alpha]_D = +63.28°$. $^1$H-NMR ($CD_3OD$) 7.48 (d, 2H, J=8.8 Hz), 6.89 (d, 2H, J=8.8 Hz), 5.51 (s, 1H), 4.72 (d, 1H, J=3.7 Hz). $^{13}$C NMR ($CD_3OD$) δ131.5, 128.8, 114.4, 103.0, 102.0, 101.4, 82.9, 75.0, 72.1, 71.6, 70.0, 63.9, 55.8. IR (KBr) 3350, 2930, 1445, 1360, 1240, 805, 607 cm$^{-1}$. Ms m/e (abundance) 312(19), 137 (100), 136 (50), 135 (80), 133 (50)<74 (32), 45 (50).

EXAMPLE 4

Methyl 4,6-0-(4-Hydroxy-3-Methoxybenzylidene) Glucopyranoside

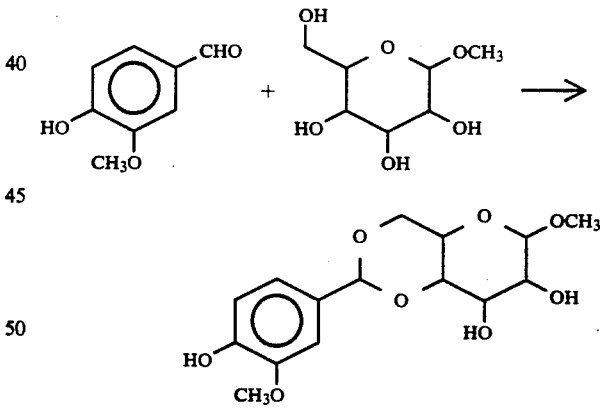

In a fashion similar to the procedure described in Example 2, vanillin and methyl glucopyranoside are combined to form methyl 4,6-O -(4-hydroxy-3-methoxybenzylidene) glucopyranoside. mp 207°–208.5° C., [α9 D= +74.5°. $^1$H-NMR ($CD_3OD$) δ7.08 (d, 1H, J=1.3 Hz), 6.93 (dd, 1H J=8.4, 1.8 Hz), 6.7 δ(d, 1H, J=8.4 Hz), 5.48 (S, 1H, 4.72.(d, 1H J=3.7 Hz), 4.26–4.12 (m, 1H), 3.84 (s, 3H), 3.83–3.58 (m, 3H), 3.55–3.37 (m, 1H), 3.42 (s, 3H), $^{13}$C NMR ($CD_3OD$) δ148.6, 148.3, 130.9, 120.6, 115.7, 103.2, 102.0, 82.9, 74.2, 72.1, 70.0, 63.9, 56.7, 55.8, IR (KBr) 3580, 3510, 3310, 3100, 2950, 2900, 1620, 1525, 1460, 1435 cm$^{-1}$. MS m/e (relative abundance) 324 (4), 328 (28), 327 (7), 311 (2), 297 (2), 225 (4), 219 (2), 152 (86), 133 (30), 45 (100).

EXAMPLE 5

4,6-O-(3,4-Methylenedioxybenzylidene) Glucose

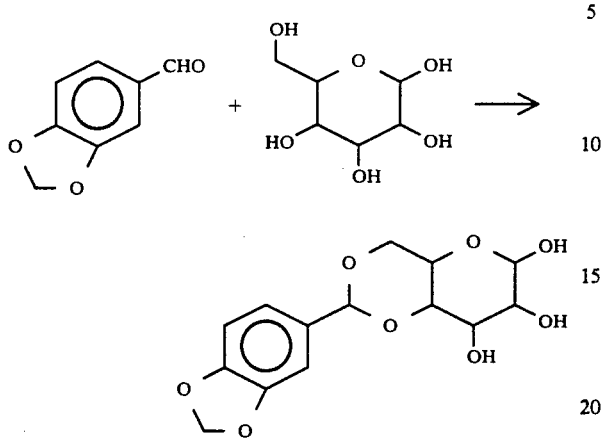

In a fashion similar to the procedure described in Example 2, piperonal and glucose combined to form 4,6-O-(3,4-methylenedioxybenzylidene) glucose. mp 172°–173° C. $[\alpha]_D = +11.4$, $^1$H-NMR (CD$_3$COCD$_3$) δ7.01–6.94 (m, 2H), 6.84–6.79 (m, 1H), 6.00 (s, 2H), 5.49 (s, 1H), 5.17 (d, 1H, J=3.6 Hz), 3.2–4.7 (m, 5H), 2.89 (broad s, 3H). IR(KBr) 3580, 2900, 1680, 1605, 1500 1445 cm$^{-1}$. MS m/e(rel. abundance) 314(I), 313(2), 312(14), 311(2), 294(2), 223(10), 149(100), 121(25), 93(30), 43(40).

EXAMPLE 6

Methyl 4,6-O-(5-Methylthiophenemethylide) Glucopyranoside

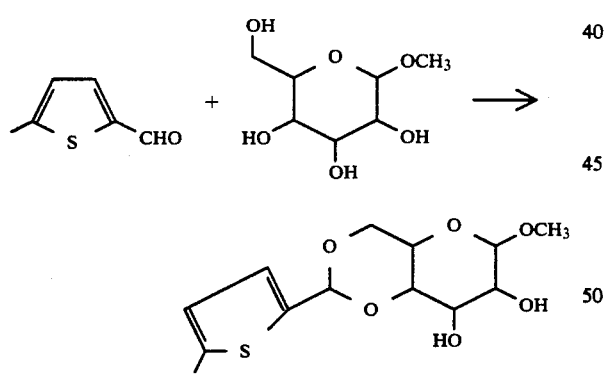

In a fashion similar to the procedure described in Example 2, 5-methylthiophenecarboxaldehyde and methyl glucopyranoside were reacted to form methyl 4,6-0-(5-methylthiophenemethylidene) glucopyranoside. mp 167°–168° C., $[\alpha]_D = +69.9°$, $^1$H-NMR (CD$_3$OD) δ6.93 (d, 1H=3.5 Hz), 6.64 (d, 1H, J=3.5 Hz), 5.74 (s, 1H), 4.72 (d, 1H, J=3.6 Hz), 4.10–4.25, (m, 1H) 3.30–3.85 (m, 5H), 3.43 (s, 3H), 2.46 (s, 3H), $^{13}$C-NMR (CD$_3$OD) δ126.75, 125.39, 102.05, 99.99, 87.12, 82.84, 74.15, 71.98, 69.97, 63.74, 55.83, 15.07, IR (KBr) 3330, 2900, 2840, 1440, 1360 cm$^{-1}$. MS m/e (% abundance) 305 (0.5), 304 (1), 303(4), 302(20), 271(2), 199 (8), 127 (100), 74 (60), 45(50).

EXAMPLE 7

Methyl 4,6-O-[3-(4-Methoxyphenyl)Prop-2-Enylidene]-Glucopyranoside

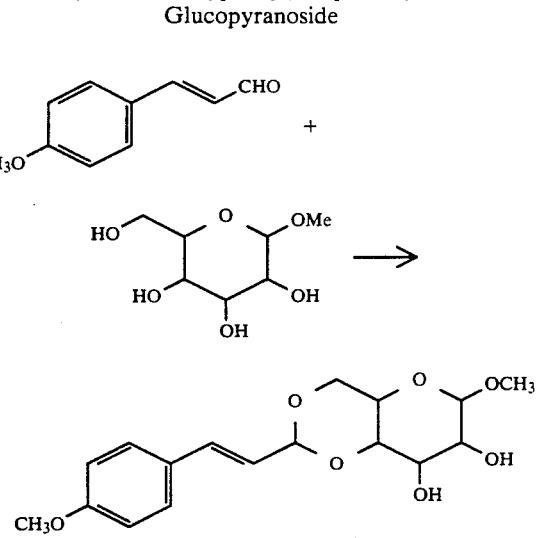

Methyl glucopyranoside and p-methoxycinnamic aldehyde were reacted in a fashion similar to that described in Example 2 to provide the product. mp 148°–150° C. $[\alpha]_D 70.0°$ (c, 1.13, methanol). $^1$H-NMR (CD$_3$OD) δ7.36 (d, 2H, J=8.9 Hz), 6.89 (d, 2H, J=8.9 Hz), 6.76 (d, 1H, J=15.7 Hz), 6.07 (dd, 2H, J=15.7 and 4.6 HZ), 5.17 (d, 1H, J=4.6 Hz), 4.7 (d, 1H, J=3.7 Hz), 4.21–4.08 (m, 1H0, 3.80 (s, 3H), 3.85–3.2 (m, 5H), 3.41 (s, 3H). $^{13}$C-NMR (CD$_3$OD) δ161.3, 134.5, 130.2, 129.0, 123.6, 115.1, 102.6, 102.0, 82.5, 74.2, 72.0, 69.7, 63.9, 55.8, IR (KBr), 3450, 1680, 1610, 1530, 1060, cm$^{-1}$. MS m/e 338, 307, 247, 179, 161, 121 (134,100%).

EXAMPLE 8

Methyl 4,6-0-(3-Phenyl-2-Pentylprop-2-Enylidene) Glucopyranoside

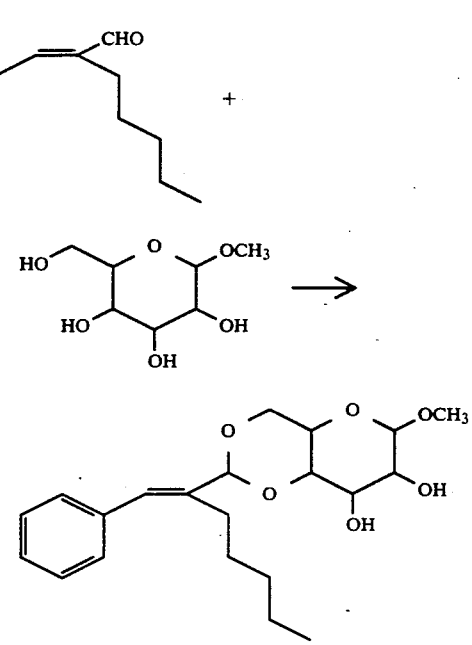

Methyl glucopyranoside and α-pentyl cinnamic aldehyde were reacted in a fashion similar to that described in Example 2 to provide the product. mp 146°–147° C. [α]$_D$ 63.5° (c, 1.36, methanol). $^1$H-NMR (CDCl$_3$) δ7.4–7.2 (m, 5H), 6.73 (s, 1H), 5.02 (s, 1H), 4.79 (d, 1H, J=4.5 Hz), 4.25 (dd, 1H, J=6.7 and 4.0), 4.0–3.35 (m, 5H), 2.95 (d, 1H, J=3.4 Hz), 2.50 (d, 1H, J=8.9 Hz), 2.34 (t, 2H, J=7.8 Hz), 1.62–1.24 (m, 6H), 0.89 (t, 3H, J=6.7 Hz). $^{13}$C-NMR (CDCl$_3$) δ138.3, 137.0, 129.2, 128.8, 126.8, 104.2, 100.0, 81.0, 73.2, 72.0, 68.9, 62.6, 55.5, 32.1, 28.6, 27.8, 22.3, 13.9. IR (KBr) 3420, 1540, 1055, 860, 740 cm$^{-1}$. MS m/e 378, 307, 287, 275 (131, 100%).

EXAMPLE 9

Methyl 4,6-0-(3-Phenyl-2-Hexylprop-2-Enylidene)-Glucopyranoside

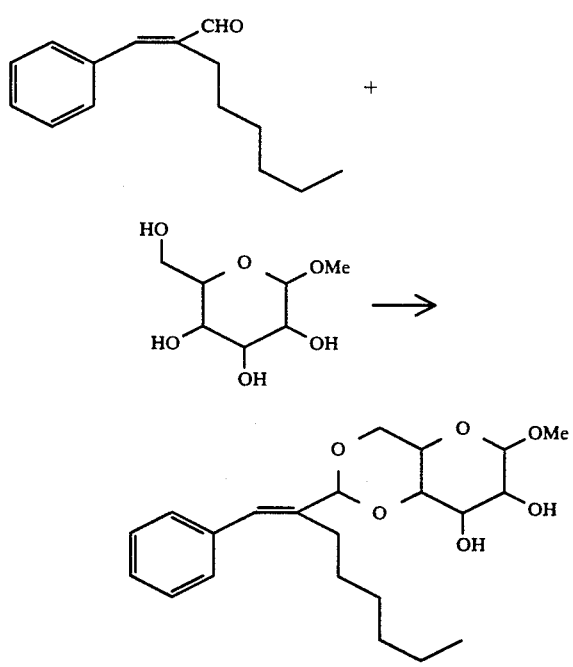

Methyl glucopyranoside and α-hexyl cinnamic aldehyde were reacted in a fashion similar to that described in Example 7 to provide the product, mp 148°–148.5° C., [δ]d 72.1° (c, 1.66 methanol). $^1$H-NMR (CDCl$_3$) δ7.36–7.15 (m, 5H), 6.72 (s, 1H), 5.06 (s, 1H), 4.71 (d, 1H, J=4 HZ), 4.19–4.13 (m, 1H), 3.83–3.15 (m, 5H), 3.43 (s, 3H), 2.36–2.28 (m, 2H), 1.65–1.1 (m, 8H), 0.87 (t, 3H, J=6.5 Hz), $^{13}$C-NMR (CD$_3$OD) δ140.0, 138.4, 130.1, 129.7, 129.2, 127.9, 105.4, 102.0, 82.7, 74.2, 72.1, 69.8, 64.0, 55.8, 32.5, 30.6, 29.8, 28.5, 23.5, 14.3, IR (KBr) 3430, 1600, 1065, 965, 750, 690 cm$^{-1}$. MS m/e 392, 363, 331, 307, 275, 241, (31, 100%).

EXAMPLE 10

Preparation of a Microwave Cake Mix Base

A microwave cake mix base was prepared by mixing the following ingredients:

| A. Ingredient | Parts |
|---|---|
| Sugar | 398.0 |
| Shortening | 50.0 |
| Emulsifying Agents | 2.0 |

-continued

| A. Ingredient | Parts |
|---|---|
| Cake Flour | 392.8 |
| Corn Syrup Solids | 50.0 |
| Dextrose | 50.0 |
| Leavening Agents | 28.2 |
| Salt | 8.5 |
| Cornstarch | 5.0 |
| Xanthan Gum | 5.0 |
| Sodium Caseinate | 1.0 |
| Flow Aid | 8.5 |
| | 1000.0 |

From this cake mix a batter was prepared using the following formula:

| B. Ingredient | Parts |
|---|---|
| Microwave Cake Mix (from Part A) | 46.46 |
| Water | 30.60 |
| Scrambled Egg | 9.56 |
| Corn Oil | 13.38 |
| | 100.00 |

0.1 g of the product of Example 1 was added to 99.9 g of the cake batter. The batter was then processed in a 650 watt microwave oven for 5 minutes. The resulting cake was determined to possess a sweet, vanilla odor and taste.

EXAMPLE 11

Preparation of Sweet Vanilla Microwave Cake Mix Base 0.1 g of the product of Example 4 was added to 99.9 g of the cake batter of Example 6. The resulting cake was determined to possess a sweet, vanilla odor and taste.

EXAMPLE 12

Preparation of Anisaldehyde Microwave Cake Mix Base 0.1 g of the product of Example 3 was added to 99.9 g of the cake batter of Example 6. The resulting cake possessed anisaldehyde odors and flavors.

EXAMPLE 13

Preparation of a Chewing Gum 0.1 g of the product of Example 3 was added to 99.9 g of chewing gum base. The resulting chewing gum possessed sweet notes due to anisaldehyde.

EXAMPLE 14

Preparation of Vanillin Cigarette

A 1% solution of the product of Example 1 in ethanol was applied to cigarette papers to produce levels of 5–50,000 ppm of the flavorant. The paper was incorporated in cigarettes and, upon burning, released a strong vanillin odor.

EXAMPLE 15

Preparation of a Cinnamaldehyde Cigarette

A 1% solution of the product of Example 2 in ethanol was applied to cigarette papers to produce levels of 5 to 50,000 ppm of the flavorant. The paper was incorporated in cigarettes and upon burning, released a strong cinnamaldehyde odor.

EXAMPLE 16

Preparation of a α-Hexylcinnamaldehyde Cigarette

A 1% solution of the produce of Example 9 in ethanol was applied to cigarette papers to produce levels of 5 to 50,000 ppm of the flavorant. The paper was incorporated in cigarettes and upon burning, released a strong floral jasmine-like odor with a herbal note.

EXAMPLE 17

Preparation of a Cigarette Containing a Vanillin Flavored Tobacco

A 1% solution of the product of Example 1 in ethanol was injected onto the tobacco of a typical American Blend Cigarette at a level of 100 ppm. Prior to smoking, no odor of vanillin was observed. Upon smoking, the mainstream and sidestream smoke displayed a strong vanillin odor.

EXAMPLE 18

Preparation of Cigarette Containing α-Hexylcinnamaldehyde Flavored Tobacco

A 1% solution of the product of Example 9 in ethanol was injected onto the tobacco of a typical American Blend cigarette at a level of 100 ppm. Prior to smoking, no odor due to α-hexylcinnamaldehyde was observed. Upon smoking the mainstream and sidestream smoke was less harsh than an unflavored cigarette and displayed a strong floral jasmine-like odor along with a clean fresh note.

While certain preferred embodiments have been described herein in detail, numerous alternative embodiments are contemplated as falling within the spirit of the invention. Consequently, the scope of the appended claims is not to be limited thereby.

What is claimed is:

1. A compound represented by the formula:

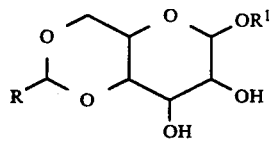

where $R^1$ is H or $C_1$ to $C_6$ alkyl;
R is Ar or $Ar^1$,
with Ar equal to 3-ethoxy-4-hydroxyphenyl or 5-methylthiophen-2-yl, and
$Ar^1$ is

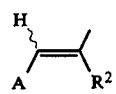

with A representing phenyl, 4-methoxyphenyl or 3-methoxy-4-hydroxyphenyl,
such that when A is phenyl, $R^2$ is $C_1$ to $C_6$ alkyl;
when A is 4-methoxyphenyl, $R^2$ is H or $C_1$ to $C_6$ alkyl; and when A is 3-methoxy-4-hydroxyphenyl, $R^2$ is H.

2. A compound as defined in claim 1 where R represents Ar.

3. A compound as described in claim 1 where R represents $Ar^1$, A represents phenyl and $R^2$ is $C_1$ to $C_6$ alkyl.

4. A compound as defined in claim 1 where R represents $Ar^1$, $Ar^1$ represents

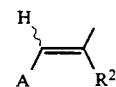

A represents 4-methoxyphenyl and $R^2$ is H.

5. A compound as defined in claim 1 where R represents $Ar^1$,
$Ar^1$ is

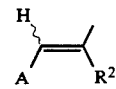

A represents 3-methoxy-4-hydroxyphenyl and $R^2$ is H.

6. A compound as defined in claim 1 having the name:
methyl 4,6-0-(4-hydroxy-3-ethoxybenzylidene) glucopyranoside;
methyl 4,6-0-(3-methoxy-4-hydroxyphenyl)prop-2-enylidene glucopyranoside;
methyl 4,6-0-(5-methylthiophenemethylide) glucopyranoside;
methyl 4,6-0-[3-(4-methoxyphenyl)prop-2-enylidene]glucopyranoside; and
methyl 4,6-0-(3-phenyl-2-pentylprop-2-enylidene) glucopyranoside or
methyl 4,6-0-(3-phenyl-2-hexylprop-2-enylidene) glucopyranoside.

7. A smoking composition which comprises natural tobacco or a tobacco substitute in combination with an organoleptically effective amount of a compound represented by the formula Ib:

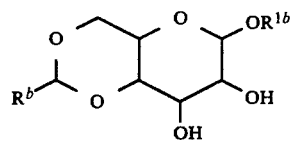

where
$R^{1b}$ represents H or $C_1$ to $C_6$ alkyl;
$R^b$ is $Ar^b$ or $Ar^{1b}$, with
$Ar^b$ equal to 3-ethoxy-4-hydroxyphenyl, 3-methoxy-4-hydroxyphenyl, 4-methoxyphenyl, 3,4-methylenedioxyphenyl or heteroaryl, and $Ar^{1b}$ is

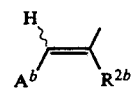

with $A^b$ equal to phenyl, 4-methoxyphenyl, 3-methoxy-4-hydroxphenyl, 3,4-methylenedioxyphenyl, or heteroaryl, and
$R^{2b}$ is H or $C_1$ to $C_6$ alkyl.

8. A smoking composition as described in claim 7 wherein the compound has the name:
methyl 4,6-0-(4-hydroxy-3-ethoxybenzylidene) glucopyranoside;
methyl 4,6-0-(3-methoxy-4-hydroxyphenyl)prop-2-enylidene glucopyranoside;
methyl 4,6-0-(5-methylthiophenemethylide) glucopyranoside;

methyl 4,6-0-[3-(4-methoxyphenyl)prop-2-enylidene]glucopyranoside;
methyl 4,6-0-(3-phenyl-2-pentylprop-2-enylidene) glucopyranoside;
methyl 4,6-0-(3-phenyl-2-hexylprop-2-enylidene) glucopyranoside;
methyl 4,6-0-(3-methoxy-4-hydroxybenzylidene) glucopyranoside;
methyl 4,6-0-(4-methoxybenzylidene)glucopyranoside;
methyl 4,6-0-(3-phenylprop-2-enylidene)-glucopyranoside;
methyl 4,6-0-(3-furanylprop-2-enylidene)-glucopyranoside;
methyl 4,6-0-(3,4-methylenedioxybenzylidene) glucopyranoside, or
methyl 4,6-0-(3-(3,4-methylenedioxyphenyl)prop-2-enylidene)glucopyranoside.

9. A smoking composition according to claim 8 wherein the concentration of said compound is between about 5 ppm and about 50,000 ppm by weight of the tobacco or tobacco substitute.

10. A media suitable for enclosing tobacco or a tobacco substitute, which contains between about 5 ppm and about 50,000 ppm of a compound having the name:
methyl 4,6-0-(4-hydroxy-3-ethoxybenzylidene) glucopyranoside;
methyl 4,6-0-(3-methoxy-4-hydroxyphenyl)prop-2-enylidene glucopyranoside;
methyl 4,6-0-(5-methylthiophenemethylide) glucopyranoside;
methyl 4,6-0-[3-(4-methoxyphenyl)prop-2-enylidene]glucopyranoside;
methyl 4,6-0-(3-phenyl-2-pentylprop-2-enylidene) glucopyranoside;
methyl 4,6-0-(3-phenyl-2-hexylprop-2-enylidene) glucopyranoside;
methyl 4,6-0-(3-methoxy-4-hydroxybenzylidene) glucopyranoside;
methyl 4,6-0-(4-methoxybenzylidene)glucopyranoside;
methyl 4,6-0-(3-phenylprop-2-enylidene)-glucopyranoside;
methyl 4,6-0-(3-furanylprop-2-enylidene)-glucopyranoside;
methyl 4,6-0-(3,4-methylenedioxybenzylidene) glucopyranoside, or
methyl 4,6-0-(3-(3,4-methylenedioxyphenyl)prop-2-enylidene)glucopyranoside.

11. A food product comprising a foodstuff in combination with an amount of a compound represented by formula Ia:

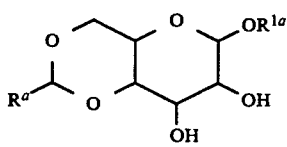

where
$R^{1a}$ represents H or $C_1$ to $C_6$ alkyl;
$R^a$ is $Ar^a$ or $Ar^{1a}$, with
$Ar^a$ representing 3-ethoxy-4-hydroxyphenyl, 3-methoxy-4-hydroxyphenyl, 4-methoxyphenyl or heteroaryl,
and $Ar^{1a}$ represents

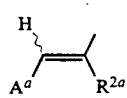

with $A^a$ representing phenyl, 4-methoxyphenyl, 3-methoxy-4-hydroxyphenyl or heteroaryl, and $R^{2a}$ representing H or $C_1$ to $C_6$ alkyl.

12. A food product according to claim 11 wherein the compound is present in a amount ranging from about 0.05% to about 5.00% by weight.

13. A food product as described in claim 11 comprising a baked foodstuff in combination with a compound as described therein in an amount effective for imparting flavor to said foodstuff upon baking.

14. A baked food product according to claim 13 wherein the amount of said compound present in the foodstuff product ranges from about 0.05% to about 5.00% by weight.

15. A food product as described in claim 11 further comprising a microwavable foodstuff in combination with a compound as described therein in an amount effective for imparting flavor to said foodstuff upon microwave cooking.

16. A microwavable food product according to claim 15 wherein the concentration of said compound is between about 0.05% and 5.00% by weight.

17. A microwave food product according to claim 15 wherein said foodstuff is a cake, cookie, cracker, bread, or toasted cereal.

18. A chewing gum base composition comprising a gum base in combination with a compound represented by formula Ia:

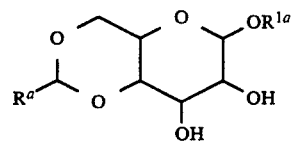

where
$R^{1a}$ represents H or $C_1$ to $C_6$ alkyl;
$R^a$ is $Ar^a$ or $Ar^{1a}$, with
$Ar^a$ representing 3-ethoxy-4-hydroxyphenyl, 3-methoxy-4-hydroxyphenyl, 4-methoxyphenyl or heteroaryl,
and $Ar^{1a}$ represents

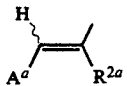

with $A^a$ representing phenyl, 4-methoxyphenyl, 3-methoxy-4-hydroxyphenyl or heteroaryl, and $R^{2a}$ representing H or $C_1$ to $C_6$ alkyl.
said compound being present in an amount effective for imparting flavor to said gum base upon mastication thereof.

19. A chewing gum base according to claim 18 wherein the amount of said compound present in said gum base ranges from about 0.1% to about 10.0% by weight.

20. A method of flavoring a food comprising treating a food with an organoleptically effective amount of a compound of the formula I:

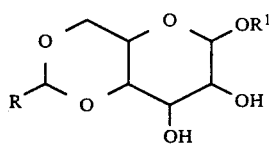

where $R^1$ is H or $C_1$ to $C_6$ alkyl;
R is Ar or $Ar^1$,
with Ar equal to 3-ethoxy-4-hydroxyphenyl or 5-methylthiophen-2-yl, and $Ar^1$ is

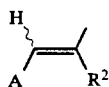

wherein A represents phenyl, 4-methoxyphenyl or 3-methoxy-4-hydroxyphenyl,
such that when A is phenyl, $R^2$ is $C_1$ to $C_6$ alkyl;
when A is 4-methoxyphenyl, $R^2$ is H or $C_1$ to $C_6$ alkyl, and when A is 3-methoxy-4-hydroxyphenyl, $R^2$ is H.

21. The method of claim 20 wherein the food is a microwavable food.

22. A method of flavoring a chewing gum base comprising adding to the chewing gum base an organoleptically effective amount of a compound of formula I:

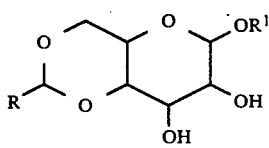

wherein $R^1$ is H or $C_1$ to $C_6$ alkyl;
R is Ar or $Ar^1$,
with Ar equal to 3-ethoxy-4-hydroxyphenyl or 5-methylthiophen-2-yl, and $Ar^1$ is

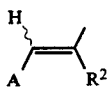

with A representing phenyl, 4-methoxyphenyl or 3-methoxy-4-hydroxyphenyl,
such that when A is phenyl, $R^2$ is $C_1$ to $C_6$ alkyl:
when A is 4-methoxyphenyl, $R^2$ is H or $C_1$ to $C_6$ alkyl, and when A is 3-methoxy-4-hydroxyphenyl, $R^2$ is H.

23. A method of flavoring tobacco comprising adding to the tobacco an organoleptically effective amount of a compound of formula I:

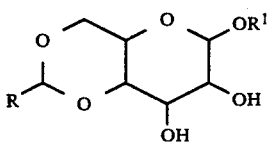

wherein $R^1$ is H or $C_1$ to $C_6$ alkyl;
R is Ar or $Ar^1$,
with Ar equal to 3-ethoxy-4-hydroxyphenyl or 5-methylthiophen-2-yl, and $Ar^1$ is

with A representing phenyl, 4-methoxyphenyl or 3-methoxy-4-hydroxyphenyl,
such that when A is phenyl, $R^2$ is $C_1$ to $C_6$ alkyl;
when A is 4-methoxyphenyl, $R^2$ is H or $C_1$ to $C_6$ alkyl, and when A is 3-methoxy-4-hydroxyphenyl, $R^2$ is H.

24. A method of flavoring a smoking composition comprising treating tobacco or a tobacco substitute with an organoleptically effective compound having the name:

methyl 4,6-0-(4-hydroxy-3-ethoxybenzylidene) glucopyranoside;
methyl 4,6-0-(3-methoxy-4-hydroxyphenyl)prop-2-enylidene glucopyranoside;
methyl 4,6-0-(5-methylthiophenemethylide) glucopyranoside;
methyl 4,6-0-[3-(4-methoxyphenyl)prop-2-enylidene] glucopyranoside;
methyl 4,6-0-(3-phenyl-2-pentylprop-2-enylidene) glucopyranoside;
methyl 4,6-0-(3-phenyl-2-hexylprop-2-enylidene) glucopyranoside;
methyl 4,6-0-(3-methoxy-4-hydroxybenzylidene) glucopyranoside;
methyl 4,6-0-(4-methoxybenzylidene) glucopyranoside;
methyl 4,6-0-(3-phenylprop-2-enylidene) glucopyranoside;
methyl 4,6-0-(3-furanylprop-2-enylidene) glucopyranoside;
methyl 4,6-0-(3,4-methylenedioxybenzylidene) glucopyranoside, or
methyl 4,6-0-(3-(3,4-methylenedioxyphenyl)prop-2-enylidene)glucopyranoside.

25. A method of flavoring a smoking composition which comprises natural tobacco or a tobacco substitute comprising treating the tobacco or tobacco substitute with an organoleptically effective amount of a compound represented by the formula Ib:

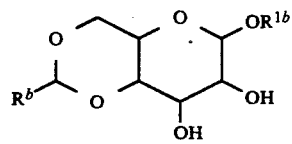

where $R^{1b}$ represents H or $C_1$ to $C_6$ alkyl;
$R^b$ is $Ar^b$ or $Ar^{1b}$, with
$Ar^b$ equal to 3-ethoxy-4-hydroxyphenyl, 3-methoxy-4-hydroxyphenyl, 4-methoxyphenyl, 3,4-methylenedioxyphenyl or heteroaryl, and $Ar^{1b}$ is

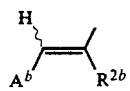

with $A^b$ equal to phenyl, 4-methoxyphenyl, 3-methoxy-4-hydroxyphenyl, 3,4-methylenedioxyphenyl, or heteroaryl, and
$R^{2b}$ is H or $C_1$ to $C_6$ alkyl.

26. A method according to claim 25 wherein the concentration of said compound is between about 5 ppm and about 50,000 ppm by weight of the tobacco or tobacco substitute.

27. A method of flavoring a medium suitable for enclosing tobacco or a tobacco substitute, comprising treating said medium with between about 5 ppm and about 50,000 ppm of a compound having the name:

methyl 4,6-0-(4-hydroxy-3-ethoxybenzylidene) glucopyranoside;
methyl 4,6-0-(3-methoxy-4-hydroxyphenyl)prop-2-enylidene glucopyranoside;
methyl 4,6-0-(5-methylthiophenemethylide) glucopyranoside;
methyl 4,6-0-[3-(4-methoxyphenyl)prop-2-enylidene] glucopyranoside;
methyl 4,6-0-(3-phenyl-2-pentylprop-2-enylidene) glucopyranoside;
methyl 4,6-0-(3-phenyl-2-hexylprop-2-enylidene) glucopyranoside;
methyl 4,6-0-(3-methoxy-4-hydroxybenzylidene) glucopyranoside;
methyl 4,6-0-(4-methoxybenzylidene) glucopyranoside;
methyl 4,6-0-(3-phenylprop-2-enylidene) glucopyranoside;
methyl 4,6-0-(3-furanylprop-2-enylidene) glucopyranoside;
methyl 4,6-0-(3,4-methylenedioxybenzylidene) glucopyranoside, or
methyl 4,6-0-(3-(3,4-methylenedioxyphenyl)prop-2-enylidene)glucopyranoside.

28. A method of flavoring a food product comprising treating a foodstuff with an organoleptically effective amount of a compound represented by formula Ia:

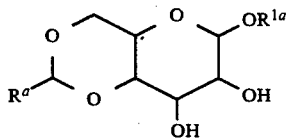

Ia where $R^{1a}$ represents H or $C_1$ to $C_6$ alkyl;
$R^a$ is $Ar^a$ or $Ar^{1a}$, with
$Ar^a$ representing 3-ethoxy-4-hydroxyphenyl, 3-methoxy-4-hydroxyphenyl, 4-methoxyphenyl or heteroaryl,
and $Ar^{1a}$ represents

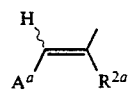

with $A^a$ representing phenyl, 4-methoxyphenyl, 3-methoxy-4-hydroxyphenyl or heteroaryl, and $R^{2a}$ representing H or $C_1$ to $C_6$ alkyl.

29. A method according to claim 28 wherein the compound is present in an amount ranging from about 0.05% to about 5.00% by weight.

30. A method as described in claim 28 further comprising baking the foodstuff in combination with a compound as described therein in an amount effective for imparting flavor to said foodstuff upon baking.

31. A method of flavoring a chewing gum base composition comprising treating a gum base with an organoleptically effective amount of a compound represented by formula Ia:

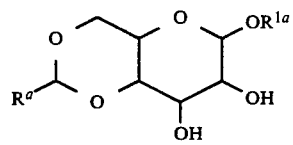

where $R^{1a}$ represents H or $C_1$ to $C_6$ alkyl;
$R^a$ is $Ar^a$ or $Ar^{1a}$, with
$Ar^a$ representing 3-ethoxy-4-hydroxyphenyl, 3-methoxy-4-hydroxyphenyl, 4-methoxyphenyl or heteroaryl,
and $Ar^{1a}$ represents

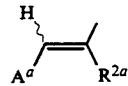

with $A^a$ representing phenyl, 4-methoxyphenyl, 3-methoxy-4-hydroxyphenyl or heteroaryl, and $R^{2a}$ representing H or $C_1$ to $C_6$ alkyl.
said compound being present in an amount effective for imparting flavor to said gum base upon mastication thereof.

32. A method according to claim 30 wherein the amount of said compound present in said gum base ranges from about 0.1% to about 10.0% by weight.

* * * * *